(12) United States Patent
Song et al.

(10) Patent No.: US 8,598,375 B2
(45) Date of Patent: Dec. 3, 2013

(54) METHOD OF PREPARING DICHLOROPROPANOL USING GLYCEROL WITH IMPROVED SELECTIVITY FOR DICHLOROPROPANOL

(75) Inventors: Won Seob Song, Ulsan (KR); Sung Yul Woo, Ulsan (KR); Boo Weon Song, Ulsan (KR); Seong Han Park, Ulsan (KR); Sung Jin Park, Ulsan (KR); Hong Tae Song, Ulsan (KR); Myoung Suk Kwon, Ulsan (KR)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 110 days.

(21) Appl. No.: 13/142,186

(22) PCT Filed: Feb. 18, 2009

(86) PCT No.: PCT/KR2009/000770
§ 371 (c)(1),
(2), (4) Date: Jun. 24, 2011

(87) PCT Pub. No.: WO2010/076914
PCT Pub. Date: Jul. 8, 2010

(65) Prior Publication Data
US 2011/0282080 A1    Nov. 17, 2011

(30) Foreign Application Priority Data

Dec. 31, 2008 (KR) ........................ 10-2008-0138708

(51) Int. Cl.
*C07D 301/27* (2006.01)
*C07C 31/34* (2006.01)

(52) U.S. Cl.
USPC ............................................ 549/514; 568/841

(58) Field of Classification Search
USPC .......................................... 568/841; 549/514
See application file for complete search history.

(56) References Cited

U.S. PATENT DOCUMENTS

| | | | |
|---|---|---|---|
| 3,878,261 A | 4/1975 | Gardner | |
| 4,973,763 A | 11/1990 | Jakobson | |
| 2007/0112224 A1 | 5/2007 | Krafft | |
| 2007/0167659 A1* | 7/2007 | Kubicek et al. | ............... 568/841 |
| 2008/0281132 A1 | 11/2008 | Krafft | |

FOREIGN PATENT DOCUMENTS

| | | |
|---|---|---|
| CN | 1882522 A | 12/2006 |
| EP | 0518765 B1 | 12/1994 |

(Continued)

OTHER PUBLICATIONS

International Search Report, PCT/KR2009/000770, mailed Sep. 16, 2009.

(Continued)

*Primary Examiner* — Taylor Victor Oh
(74) *Attorney, Agent, or Firm* — Nixon Peabody LLP

(57) ABSTRACT

A method of preparing dichloropropanol using glycerol. The method includes: chlorination of glycerol including a plurality of chlorination reaction stages using a catalyst; and a water-removing stage performed between the reaction stages, independently of the reaction stages.

6 Claims, 2 Drawing Sheets

(56) References Cited

FOREIGN PATENT DOCUMENTS

| | | |
|---|---|---|
| JP | 2007-511583 A | 2/2007 |
| JP | 2007-504101 A | 3/2007 |
| JP | 2007-277261 A | 10/2007 |
| KR | 1020060130775 A | 12/2006 |
| WO | 20051021476 A1 | 3/2005 |
| WO | 2005/054167 A1 | 6/2005 |
| WO | 20051054167 A1 | 6/2005 |
| WO | 20081128005 A1 | 10/2008 |

OTHER PUBLICATIONS

Written Opinion of the International Searching Authority, PCT/KR2009/000770, mailed Sep. 17, 2009.
Non-Final Rejection, KR10-2008-0138708, dated Dec. 20, 2010, (w/translation).
Chinese Office Action in Chinese Application No. 200980153095.8, mailed on May 6, 2013.
Office Action for Japanese Application No. 2011-543377, mailed on Jul. 23, 2013.

\* cited by examiner

METHOD OF PREPARING DICHLOROPROPANOL USING GLYCEROL WITH IMPROVED SELECTIVITY FOR DICHLOROPROPANOL

CROSS REFERENCE TO RELATED APPLICATIONS OR PRIORITY CLAIM

This application is a National Phase of PCT/KR2009/000770, filed Feb. 18, 2009, entitled, "METHOD OF PREPARING DICHLOROPROPANOL USING GLYCEROL WITH IMPROVED SELECTIVITY FOR DICHLOROPROPANOL", and which claims priority of, Korean Patent Application No. 10-2008-0138708, filed Dec. 31, 2008, the contents of which are incorporated herein by reference in their entirety.

TECHNICAL FIELD

An embodiment of the present invention relates to a method of preparing dichloropropanol using glycerol, and more particularly, to a method of preparing dichloropropanol including: performing a plurality of chlorination reactions of glycerol using a catalyst and producing water as a by-product; and performing a water-removing stage between the chlorination reactions, independently of the chlorination reactions.

BACKGROUND ART

Recently, bio-diesels have been competitively developed and produced worldwide, and also domestically manufactured and brought to markets as an additive to petro-diesel.

During the production of bio-diesel, a large amount of glycerol, corresponding to about 10% of the amount of the produced bio-diesel, is generated as a by-product. However, supply of glycerol is greater than demand therefor and oversupply of glycerol decreases its value. Thus, it is economically advantageous to convert glycerol into dichloropropanol which is a higher-value added product compared to glycerol.

Meanwhile, dichloropropanol is a raw material used to produce epichlorohydrin. Most of the dichloropropanol which is currently supplied to markets is manufactured from propylene. More particularly, a method of preparing dichloropanol includes a two-stage process of preparing allyl chloride through high temperature chlorination of propylene and preparing dichloropropanol by reacting the allyl chloride with hydrochloric acid using an excess amount of industrial water. However, the method of preparing dichloropropanol using propylene has problems in terms of instability of propylene supply and demand caused by increased price of propylene, generation of a large amount of waste water and other waste, excessive initial investment costs due to the two-stage manufacturing process and difficulty of newly constructing/modifying the process.

Accordingly, a single-stage process of directly preparing dichloropropanol by reacting glycerol and a chlorinating agent in the presence of a catalyst is more economical. The single-stage process using glycerol is advantageous in that costs of raw materials can be reduced by using inexpensive glycerol as a reactant, the amount of waster water and other waste can be dramatically reduced since industrial water is not required for the process, and thus the process is environmentally friendly, and initial investment costs related to the process and environment can be reduced. In addition, in the single-stage process of preparing dichloropropanol from glycerol, since dichloropropanol is directly prepared from glycerol which is a by-product generated in the preparation of bio-diesels, the single-stage process is more environmentally friendly than the conventional method of preparing dichloropropanol through the two-stage manufacturing process described above.

However, water is produced as a by-product using the method of preparing dichloropropanol using glycerol, and chlorination of glycerol may be inhibited by the water. Thus, the reaction rate may be reduced, a reaction time may be increased, and selectivity for dichloropropanol may be reduced as the reaction continues.

DISCLOSURE OF THE INVENTION

The present invention provides a method of preparing dichloropropanol, the method including; chlorination of glycerol including a plurality of reaction stages using a catalyst and a water-removing stage performed independently of the reaction stages between the reaction stages.

According to an aspect of the present invention, there is provided a method of preparing dichloropropanol, the method including: performing a plurality of chlorination reactions of glycerol using a catalyst, wherein the reactions produce water as a by-product; and performing a water-removing stage between the chlorination reactions, independently of the chlorination reactions.

In each of the chlorination reactions; a reaction product of a catalyst with glycerol may be produced, as a by-product, which may function as a catalyst for the chlorination of glycerol.

A boiling point of the reaction product of the catalyst with glycerol may be higher than that of water.

The catalyst may be acetic acid, and the reaction product of the catalyst with glycerol may be a glycerol ester of acetic acid.

The chlorination reactions may include: converting glycerol into monochloropropanediol (MCP); and converting monochloropropanediol (MCP) into dichloropropanol (DCP).

The water-removing stage may be performed when a glycerol-conversion rate is in a range of about 90 to about 100%, and a monochloropanediol-conversion rate is in a range of about 20 to about 60%.

The water-removing stage may be performed using the boiling point difference between water and materials other than water.

The chlorination reactions may include using a chlorinating agent including hydrogen chloride gas or hydrochloric acid.

The chlorination reactions may be performed in at least one reactor selected from a group consisting of a batch reactor, a semi-batch reactor, a continuous stirred tank reactor (CSTR), and a plug flow reactor.

According to another aspect of the present invention, there is provided a method of preparing epichlorohydrin (ECH) using dichloropropanol prepared by chlorination of glycerol, the method including the method of preparing dichloropropanol.

BRIEF DESCRIPTION OF THE DRAWINGS

The above and/or other aspects will become apparent and more readily appreciated from the following description of the embodiments, taken in conjunction with the accompanying drawings of which.

BEST MODE FOR CARRYING OUT THE INVENTION

Figure 1:
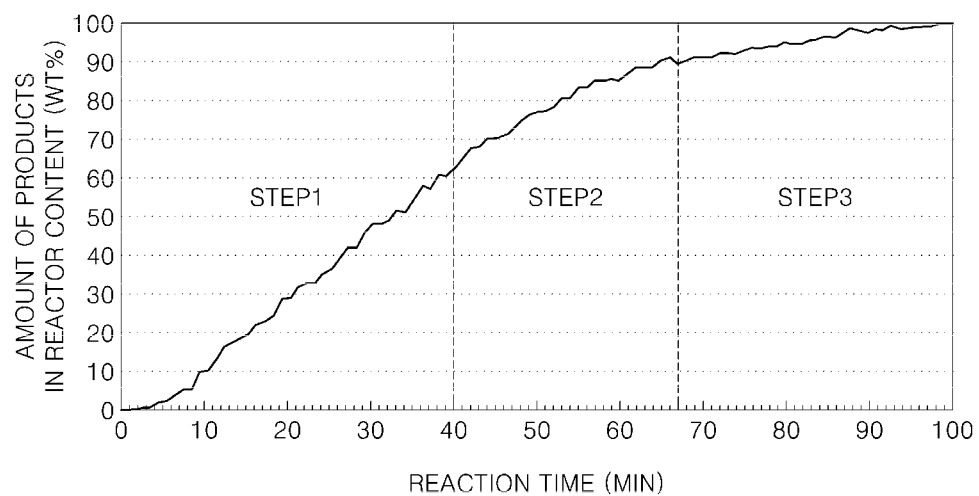
FIG. 1 is a graph illustrating weight percent changes of products in contents of a reactor over time using a conventional method of preparing dichloropropanol (Comparative Example 1)

Hereinafter, a method of preparing dichloropropanol according to an embodiment of the invention will be described in more detail with reference to the attached drawings.

A method of preparing dichloropropanol according to an embodiment includes: performing a plurality of chlorination reactions of glycerol using a catalyst, wherein the reactions produce water as a by-product; and performing a water-removing stage between the chlorination reactions, independently of the chlorination reactions. That is, water is produced as a by-product during the chlorination reactions and removed during the water-removing stage. The water-removing stage may be performed independently of the chlorination reactions. For example, since a chlorinating agent is not added to a reactor during the water-removing stage, a chlorination reaction does not occur.

During the chlorination reactions, a reaction product of a catalyst with glycerol is produced as a by-product, and the reaction product of the catalyst with glycerol may also function as a catalyst for the chlorination of glycerol. In addition, a boiling point of the reaction product of the catalyst with glycerol may be greater than that of water. Thus, if the water-removing stage is performed using the boiling point difference between water and materials including a reactant, a product other than water and/or a catalyst, reactions may be smoothly performed during the chlorination reaction stage subsequently processed after the water-removing stage without adding an additional catalyst thereto. The water-removing stage may be performed at a temperature of about 50 to about 130□ and a pressure of about 0 to about 1 bar.

For example, the catalyst may be acetic acid, and the reaction product of the catalyst with glycerol may be a glycerol ester of acetic acid.

In addition, the chlorinating agent used for the chlorination reaction may be hydrogen chloride gas or hydrochloric acid, but is not limited thereto.

In addition, the reactor used for the chlorination reaction may be a batch reactor formed of a material resistant to the chlorinating agent or a batch reactor including interior structures coated with the material resistant to the chlorinating agent. The material resistant to the chlorinating agent may be Hastelloy C or Teflon. According to the current embodiment, the chlorination reaction may be performed at a temperature in a range of about 50 to about 2000□. If the temperature is higher than 50□, the reaction rate may be high. On the other hand, if the temperature is lower than 200□, energy loss may be small. In addition, the chlorination reaction may be performed at a pressure equal to or higher than 1 bar, for example, in a range of about 1 to about 50 bar. Even though the activity is increased with the increase of the reaction pressure, the reaction activities are similar at a pressure greater than a certain level, for example, greater than 50 bar. The pressure may be controlled using an inert gas, for example, nitrogen. The reaction time may be in a range of about 10 minutes to about 100 minutes. If the reaction time is less than 10 minutes, the glycerol-conversion rate is too low. On the other hand, if the reaction time is greater than 100 minutes, the reaction is almost completed, and thus the conversion rate and selectivity are not changed.

Herein, the "dichloropropanol (DCP)" indicates a mixture of isomers including 1,3-dichloropropane-2-ol (1,3-DCP) and 1,2-dichloropropane-3-ol (1,2-DCP). According to the method of preparing dichloropropanol according to the current embodiment, 1,3-DCP is mainly produced. 1,3-DCP may be used as a reactant for the preparation of epichlorohydrin.

The chlorination reactions of glycerol are performed as Reaction Scheme 1 below.

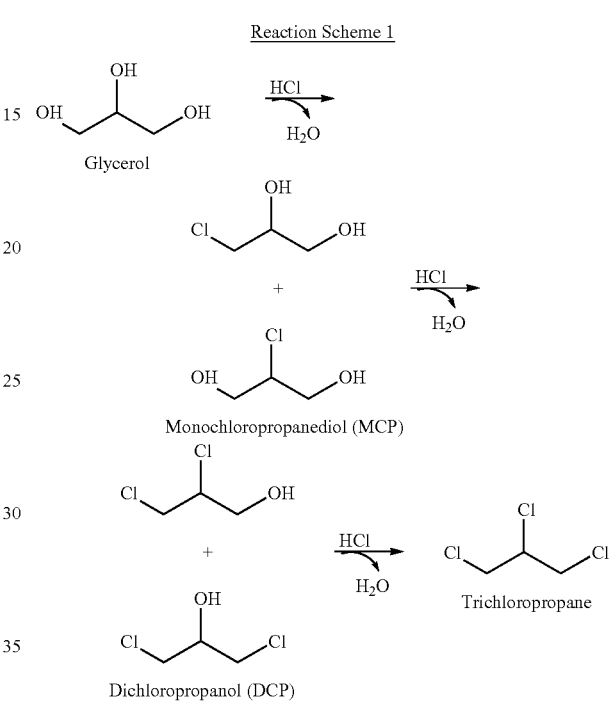

Reaction Scheme 1

The dichloropropanol may further be subjected to a reaction with alkali to prepare epichlorohydrin.

In the reaction, glycerol-conversion rates, monochloropropanediol-conversion rates, selectivities for monochloropropanediol, and selectivities for dichloropropanol may be respectively calculated using Equations 1 to 4 below.

Glycerol-conversion rate (%)=(the number of moles of reacted glycerol/the number of moles of supplied glycerol)×100   Equation 1

Monochloropropanediol-conversion rate (%)=(the number of moles of reacted monochloropropanediol/the number of moles of produced monochloropropanediol)×100   Equation 2

Selectivity for monochloropropanediol (%)=(the number of moles of produced monochloropropanediol/the number of moles of reacted glycerol)×100   Equation 3

Selectivity for dichloropropanol (%)=(the number of moles of produced dichloropropanol/the number of moles of reacted glycerol)×100   Equation 4

Selectivity for dichloropropanol is calculated based on a mixture of isomers including 1,3-DCP and 1,2-DCP.

The chlorination reaction according to Reaction Scheme 1 may be performed in at least one reactor selected from a group consisting of a batch reactor, a semi-batch reactor, a continuous stirred tank reactor (CSTR), and a plug flow reactor.

FIG. 1 is a graph illustrating weight percents of products in contents of a reactor with over time according to a conventional method of preparing dichloropropanol. That is, the vertical axis of the graph represents a weight percent of the amount of products as a proportion of the total amount of reactants and products. In order to produce FIG. 1 and get glycerol-conversion rate and monochloropropanediol-conversion rate described below, experiments and analyses are performed in the same manner as in Comparative Example 1 which will be described later. In particular, FIG. 1 is a graph illustrating weight percents of products of the reactor contents over time when reactions as shown in Reaction Scheme 1 above are continuously performed in a batch reactor without removing water which is produced as a by-product.

Referring to FIG. 1, chlorination reaction of glycerol may be divided into three stages according to the slope of the graph corresponding to reaction rate: first stage (0 to 40 minutes); second stage (40 to about 67 minutes); and third stage (about 67 to 100 minutes.

In the first stage, an average slope angle of the graph is about 45°, a glycerol-conversion rate is equal to or less than 90%, and a monochloropropanediol-conversion rate is equal to or less than 20%. In the second stage, an average slope angle of the graph is about 35°, a glycerol-conversion rate is in a range of about 90 to about 100%, and a monochloropropanediol-conversion rate is in a range of about 20 to about 60%. In the third stage, an average slope angle of the graph is about 11°, a glycerol-conversion rate is 100%, and a monochloropropanediol-conversion rate is equal to or greater than 60%.

That is, since the reaction rate is gradually reduced after the reaction is initiated, the reaction rate and the yield of DCP may be increased by removing water, which inhibits the reaction, during the first stage, right after the first stage, during the second stage, and after the second stage in a state such that the reaction is not performed, and performing subsequent reaction stages.

In particular, when the chlorination reaction is performed in a batch reactor and/or a semi-batch reactor, the amount of the chlorinating agent may be controlled in advance so that the chlorination reaction is not continued after a predetermined period of time, for example, after the first stage, and then water is removed. After the water is removed, the temperature and the pressure are appropriately regulated and a predetermined amount of the chlorinating agent is further added to the reactor in order to perform a subsequent reaction stage, e.g., the second stage.

Meanwhile, if the chlorination reaction is performed in a continuous stirred tank reactor (CSTR) and/or a plug flow reactor, the size of the reactors may also be controlled while regulating the temperature and the pressure to prepare dichloropropanol. For example, a first reactor in which the first stage reaction is performed, a distillation column in which water is removed, and a second reactor in which the second stage reaction is performed may be used.

For example, the water-removing stage may be performed when the glycerol-conversion rate is in a range of about 90 to about 100%, and the monochloropropanediol-conversion rate is in a range of about 20 to about 60%. If the glycerol-conversion rate is less than 90%, and the monochloropropanediol-conversion rate is less than 20%, the total amount of water produced as a by-product is too little, and thus the influence of water on the reaction rate is negligible. On the other hand, if the glycerol-conversion rate is greater than 90%, and the monochloropropanediol-conversion rate is greater than 20%, the total amount of water produced as a by-product is too large, and thus the reaction rate may be reduced. In addition, if the monochloropropanediol-conversion rate is greater than 60%, the total amount of water produced as a by-product is too large, and thus the reaction rate may be significantly reduced, and selectivity for dichloropropanol may also be reduced.

According to the method of preparing dichloropropanol as described above, the reduction in the reaction rate may be inhibited, and the selectivity for dichloropropanol may be increased by removing water, as a by-product, without losing the chlorinating agent and/or the catalyst.

Meanwhile, a method of preparing epichlorohydrin including the method of preparing dichloropropanol may be provided according to an embodiment of the present invention.

The present invention will be described in more detail with reference to the examples below. However, these examples are for illustrative purposes only and are not intended to limit the scope of the invention.

EXAMPLES

Preparation of Dichloropropanol from Glycerol in the Presence of Acetic Acid Catalyst Experimental Example 1(=Comparative Example)

Without Water-removing Stage

Figure 2:
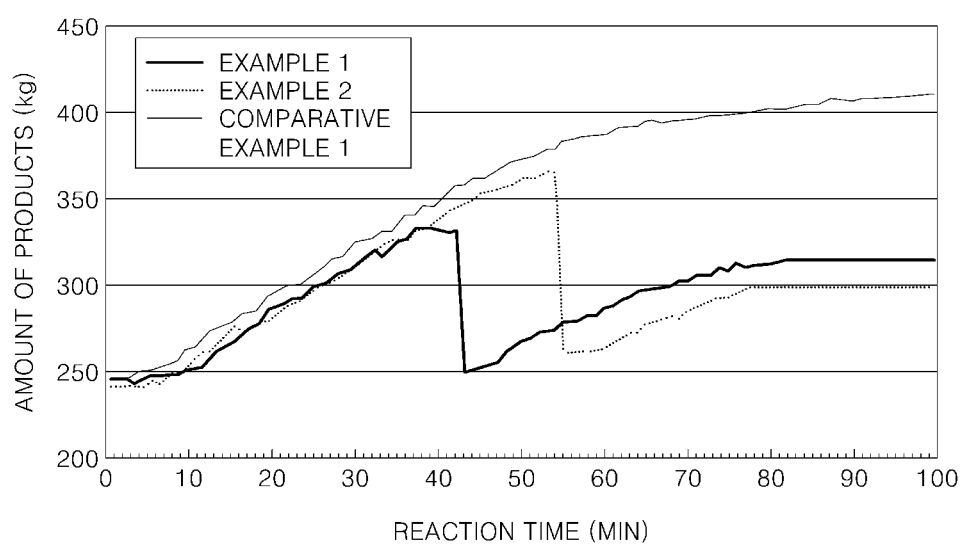
FIG. 2 is a graph illustrating weight percent changes of products with a lapse of time using methods of preparing dichloropropanol according to Examples 1 and 2 and Comparative Example 1.

Dichloropropanol was prepared from glycerol using an acetic acid catalyst. The reaction was performed in a semi-batch reactor having a volume of 650 L in a liquid phase. An inner structure of the semi-batch reactor was formed of a glass lining and Teflon which are resistant to a chlorinating agent. First, 250 kg of glycerol and 10 kg of anhydrous acetic acid were added to the semi-batch reactor. Then, the reaction was performed while maintaining the temperature at 130□, stirring, and continuously introducing 99.7% by volume of hydrogen chloride gas, as a chlorinating agent, into the semi-batch reactor at a constant pressure of 6 bar. While the reaction was performed, contents of the reactor were collected at five-minute intervals. Then, the amount of products (MCP+DCP+water, etc.) in the contents of the reactor were analyzed using gas chromatography, and the weight percent changes of the products over time were calculated. The results are shown in FIG. 2. Furthermore, glycerol-conversion rate and monochloropropanediol-conversion rate were respectively calculated using Equations 1 and 2 and recorded.

After the reaction was terminated, the reactor was cooled to room temperature, and the contents of the reactor were analyzed using gas chromatography. Then, selectivities of monochloropropanediol and dichloropropanol were respectively calculated using Equations 3 and 4 and shown in Table 1 below. The "MCP" and "DCP" of Table 1 respectively indicate monochloropropanediol and dichloropropanol. Water was produced as a by-product of the reaction. The reaction termination time was also measured and shown in Table 1 below. In this regard, the reaction termination time indicates a point of time when the weight percent change of the product over time is close to '0' in FIG. 2.

Example 1

With Water-removing Stage

A reaction was initiated in the same manner as in Experimental Example 1. When the glycerol-conversion rate reached 90%, and the monochloropropanediol-conversion rate reached 20% (using data recorded according to Experimental Example 1), water was removed from the contents of the reactor by reducing the pressure of the reactor to 200 torr and maintaining the reactor at a temperature of 130☐ for 2 minutes. After removing water, a subsequent reaction was performed while maintaining the temperature of the reactor at 130☐, stirring, and continuously introducing 99.7% by volume of hydrogen chloride gas, as a chlorinating agent, into the reactor at a constant pressure of 6 bar. After the reaction was terminated, selectivity for monochloropropanediol, selectivity for dichloropropanol, and reaction termination time were measured and/or calculated, and the results are shown in Table 1 below.

Example 2

Using Water-Removing Stage

Dichloropropanol was prepared from glycerol in the same manner as in Example 1, except that water was removed when the glycerol-conversion rate reached 99% and the monochloropropanediol-conversion rate reached 48%. After the reaction was terminated, selectivity for monochloropropanediol, selectivity for dichloropropanol, and reaction termination time were measured and/or calculated, and the results are shown in Table 1 below.

TABLE 1

|  |  | Example 1 | Example 2 | Comparative Example 1 |
|---|---|---|---|---|
| Selectivity for products (%) | 1,3-DCP | 79.8 | 81.0 | 77.2 |
|  | 2,3-DCP | 5.6 | 5.7 | 5.4 |
|  | Total DCP | 85.4 | 86.7 | 82.6 |
|  | MCP | 4.1 | 3.4 | 8.2 |
| Reaction termination time (min) |  | 82 | 78 | 100 |

Referring to Table 1, selectivity for dichloropropanol prepared according to Examples 1 and 2 was increased and reaction time thereof was reduced when compared to that of dichloropropanol prepared according to Comparative Example 1.

Furthermore, referring to FIG. 2, the weight percent of the products of Examples 1 and 2 was rapidly reduced and then gradually increased by removing water, while the weight percent of the products of Comparative Example 1 was exponentially increased since water was not removed.

While the present invention has been particularly shown and described with reference to exemplary embodiments thereof, it will be understood by one of ordinary skill in the art that various changes in form and details may be made therein without departing from the spirit and scope of the present invention as defined by the following claims.

The invention claimed is:

1. A method of preparing dichloropropanol, the method comprising:
   performing a plurality of chlorination reaction stages of glycerol using a catalyst,
      wherein the plurality of chlorination reaction stages produce water as a by-product and the catalyst is acetic acid,
      wherein, in each of the chlorination reaction stages, a reaction product of the catalyst with glycerol is produced as a by-product, which functions as a catalyst for the chlorination of glycerol, and
      wherein a boiling point of the reaction product of the catalyst with glycerol is higher than that of water; and
   performing a water-removing stage between the chlorination reaction stages, independently of the chlorination reaction stages,
      wherein the chlorination reaction stages comprise converting glycerol into monochloropropanediol (MCP) and converting monochloropropanediol (MCP) into dichloropropanol (DCP),
      wherein the water-removing stage is performed using the boiling point difference between water and materials other than water,
      wherein a chlorinating agent is added to a chlorination reaction stage prior to the water-removing stage, and a separate chlorinating agent other than a chlorinating agent originated from the chlorination reaction stage prior to the water-removing stage is not added to the water-removing stage,
      wherein a separate catalyst other than a catalyst originated from the chlorination reaction stage prior to the water-removing stage is not added to a chlorination reaction stage after the water-removing stage.

2. The method of claim 1, wherein the reaction product of the catalyst with glycerol comprises a glycerol ester of acetic acid.

3. The method of claim 1, wherein the water-removing stage is performed when a glycerol-conversion rate is in a range of about 90 to about 100%, a monochloropropanediol-conversion rate is in a range of about 20 to about 60%.

4. The method of claim 1, wherein the chlorination agent comprises hydrogen chloride gas or hydrochloric acid.

5. The method of claim 1, wherein the chlorination reaction stages are performed in at least one reactor selected from a group consisting of a batch reactor, a semi-batch reactor, a continuous stirred tank reactor (CSTR), and a plug flow reactor.

6. A method of preparing epichlorohydrin (ECH) using dichloropropanol prepared by chlorination of glycerol, the method comprising a method of preparing dichloropropanol according to claim 1.

* * * * *

UNITED STATES PATENT AND TRADEMARK OFFICE
CERTIFICATE OF CORRECTION

PATENT NO. : 8,598,375 B2  Page 1 of 1
APPLICATION NO. : 13/142186
DATED : December 3, 2013
INVENTOR(S) : Song et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Twenty-second Day of September, 2015

Michelle K. Lee
*Director of the United States Patent and Trademark Office*